United States Patent [19]

Mattison et al.

[11] Patent Number: 4,886,889

[45] Date of Patent: Dec. 12, 1989

[54] PROCESS FOR RECOVERY OF AN AMINO ACID FROM AQUEOUS MIXTURES THEREOF

[75] Inventors: Phillip L. Mattison, New Brighton; Ronald P. Wirth, Minneapolis; Michael J. Virnig, Fridley; LeRoy Krbechek, Golden Valley, all of Minn.

[73] Assignee: Henkel Corporation, Ambler, Pa.

[21] Appl. No.: 864,064

[22] Filed: May 16, 1986

[51] Int. Cl.$^4$ .................... C07D 209/20; C07D 99/12; C07D 101/02

[52] U.S. Cl. .................... 548/497; 562/448; 562/553; 562/554; 562/559; 562/562; 562/563; 562/570; 562/523; 562/576; 562/443; 562/433; 562/445; 548/344

[58] Field of Search ................ 548/497, 344; 562/448, 562/553, 554, 559, 562, 563, 570, 523, 576, 443, 445

[56] References Cited

U.S. PATENT DOCUMENTS

| | | |
|---|---|---|
| 2,681,927 | 6/1954 | McCollum et al. .................. 260/529 |
| 3,318,867 | 5/1967 | Jahnke .................. 260/210 |
| 3,928,431 | 12/1975 | Broderman et al. .................. 260/519 |
| 4,523,999 | 6/1985 | Toyoshi et al. .................. 210/639 |
| 4,536,596 | 8/1985 | Savides et al. .................. 562/443 |
| 4,584,399 | 4/1986 | Portal et al. .................. 562/443 |
| 4,661,606 | 4/1987 | Tuominen et al. .................. 548/497 |
| 4,663,048 | 5/1987 | Tanaka et al. .................. 210/638 |

FOREIGN PATENT DOCUMENTS

| | | |
|---|---|---|
| 73381 | 8/1982 | European Pat. Off. . |
| 166992 | 6/1985 | European Pat. Off. . |
| 2557104 | 12/1984 | France . |
| 2562067 | 3/1985 | France . |
| 58-57158 | 12/1983 | Japan . |
| 59-23797 | 6/1984 | Japan . |

OTHER PUBLICATIONS

*Chemical Abstracts,* 80:99915p.

JACS, 95:18; Sep. 5, 1973, pp. 6108–6110, Transport of Amino Acids Through Organic Liquid Membranes, Behr and Lehn.

Chem. Ind. XXXVI, pp. 458–461, Aug. 1984; Reaktiveatraktion von Salicylsaure und d,1-Phenylalanin, with CA 103:217253, abstract.

Chem. Eng. Sci. 41, No. 7, pp. 1811–1815, 1986, Reactive Extraction od d,1-phenylalanine with Trioctyl-methyl-ammonium chloride as a Carrier, Haensel, Halwachs & Schugerl.

Chem. Eng. Comm. 1987, vol. 51, pp. 193–205; Reactive Extraction of Salicyclic Acid and d,1-phenylalanine in a Stirred Cell, Schlichting, Halwachs & Schugerl.

Acta. Pharm. Suec. 12, 407–416, (1975), Quantitative Determinations by Ion Pair Extraction, Part 12, Extraction of Amino Acids With Quaternary Ammonium Ions, Nordgren & Modin.

*Primary Examiner*—David B. Springer
*Attorney, Agent, or Firm*—Ernest G. Szoke; Wayne C. Jaeschke; Patrick J. Span

[57] ABSTRACT

Disclosed is a process for recovery of amino acids from aqueous mixtures. In particular, it relates to a treatment of said amino acid containing aqueous mixture prior to extraction of the amino acid with a water immiscible organic solution containing a water insoluble extractant for said amino acid. The overall process of the invention which includes the pretreatment and extraction, also includes optional methods of recovering said extracted amino acid from the water immiscible organic solution. Accordingly, the invention also relates to a process for recovery of the amino acid by stripping of the amino acid from the organic solution and precipitation of the amino acid.

33 Claims, No Drawings

PROCESS FOR RECOVERY OF AN AMINO ACID FROM AQUEOUS MIXTURES THEREOF

BACKGROUND OF THE INVENTION

1. Field of the Invention

This invention relates to a process for recovery of amino acids from aqueous mixtures. In particular, it relates to a treatment of said amino acid containing aqueous mixture prior to extraction of the amino acid with a water immiscible organic solution containing a water insoluble extractant for said amino acid. The overall process of the invention which includes the pretreatment and extraction, also includes optional methods of recovering said extracted amino acid from the water immiscible organic solution. Accordingly, this invention also relates to a process for recovery of the amino acid by stripping of the amino acid from the organic solution.

2. Description of Related Art

Amino acids, essential to animal and human nutrition are important as food additives, feed supplements, artificial sweeteners, and intravenous solutions; thus production and purification of amino acids is an important procedure. Descriptively, amino acids are organic acids containing an amino group. These compounds can be obtained by hydrolysis of a protein, by organic synthesis, or by fermentation. As a general rule, all naturally occurring amino acids are alpha-amino acids, having the —NH$_2$ group attached to the carbon atom next to the COOH group, beta-alanine being an exception to this generalization. Some amino acids are termed essential meaning that they are required for an organism's growth, but can not be synthesized by its body. Essential amino acids for human beings are: arginine, histidine, isoleucine, leucine, lysine, methionine, phenylalanine, threonine, tryptophan, and valine.

Due to present industrial procedures, it is necessary to remove amino acids from dilute fermentation broths and other aqueous mixtures. Current methods used to remove and purify amino acids are crystallization, chromatography, ion-exchange, and extraction. One such method, described in U.S. Pat. No. 2,894,954 teaches that amino acids can be removed as a solute in N-hexylamine by a plurality of liquid/liquid contacting zones. In accordance with this method the N-hexylamine is then separated from the amino acids.

Another extraction method used to separate amino acids from fermentation broths and other aqueous mixtures is discussed in: "Quantitative determinations by ion pair extraction", *ACLA PHARM. SNEC.* 12, 407–416 (1975), by Thomas Nordgren, and Rolf Modine which teaches the extraction of amino acids from fermentation broths by combining a water soluble extractant, tetrapentylammoniumiodide with an aqueous phase containing amino acids, and subsequently washing with methylene chloride. This method, disadvantageously has a tendency to leave water soluble ion pairs formed by the combination of extractant and amino acid in the aqueous phase, which are not extracted in the organic phase.

Another extraction method of recovering amino acids from aqueous mixtures is commonly assigned co-pending U.S. patent application Ser. No. 617,767, filed June 6, 1984, by Tuominen et al. now U.S. Pat. No. 4,661,606. In this Application is disclosed a process for extraction of amino acids from aqueous solutions containing at least one amino acid with a solution of a water insoluble extractant in a water immiscible organic solution. Two phases are formed, an organic phase containing the extracted amino acid and an aqueous phase, containing the non-amino acid materials. The two phases which are immiscible are then separated and the amino acid is then recovered from the organic phase. The amino acid is recovered either by precipitation or stripping from the organic solution into a second aqueous solution from which the amino acid can be recovered by conventional purification methods.

A method of isolating L-dopa from aqueous solutions thereof employing a sulfonic acid as a liquid ion exchanger can be seen in U.S. Pat. No. 3,928,431. In this method however, sulfonic acids such as dodecylbenzene sulfonic acid, a water soluble surfactant is employed. Such material is also disclosed as a surfactant in European Patent Publication No. 73381.

Such European Patent Publication further describes several aqueous mixtures containing amino acids, which are obtained during the fermentative production of amino acids. As set forth therein, reference is made to "Chem. Abstr. 76, P 57 722k; 78, P 122655y; 78, R 146 210a; 82, P 15274j and 85, P 121 806f), L-tyrosine (see, for example, Chem. Abstr. 76, P 84 566n; 77, P 60 057y; 78, R 146 210a; 82, P 17 199 m and 85, P121 806f), 3-hydroxy-L-tyrosine=DOPA (see, for example, Chem. Abstr. 76, P 152 037z; 78, P 157 879b; 80, 144 375a; 81, P 3 699f and 83, P 7 116q), L-tryptophane (see, for example, Chem. Abstr. 78, P 56 436z, R 146 220d; 81, P 13 463m; 84, 15 655a) and 5-hydroxy-L-tryptophane (see, for example, Chem. Abstr. 76, P 139 064m; 79, P 103 669; 80, P 13 649v; 80, P 106 876g and 83, 106 65s). It is basically possible to extract the actual aqueous microorganism cultures thus obtained, but it is usually more advantageous to filter or centrifuge these before extracting and to further process the solutions obtained".

BRIEF DESCRIPTION

This invention has several aspects to an overall process which includes (A) a pretreatment process prior to extraction;

(B) extraction of the amino acid with an organic solution; and (C) a process of recovery of the amino acid from the organic extractant solution.

The pretreatment process prior to extraction involves either or both of two treatments or processes:

(a) an ultrafiltration and/or (b) an adsorption treatment.

The preferred treatment is an ultrafiltration employing a membrane having a molecular weight cut off high enough to permit passage of the amino acids, but low enough to prevent passage of cellular materials, tars, other solids, etc. The amino acid can then be recovered from the diffusate by extraction with an appropriate extractant, as described in commonly assigned, co-pending Application Ser. No. 617,767 now U.S. Pat. No. 4,661,606 noted earlier above. In this process an amino acid containing aqueous solution, such as an amino acid fermentation broth (such as those noted in EP Publication No. 73881), is placed on one side of an appropriate membrane having the desired pore size, with water (i.e. deionized water) or other appropriate liquid media employed as the diffusate on the other side of the membrane. After a time sufficient for the amino acid to diffuse through the membrane, the diffusate may then be contacted with a water insoluble extractant in a water immiscible organic solution. Instead of employing water as a diffusate media, diffusion and extraction may be concurrent by the use of the organic solution containing the extractant as the diffusate media. Thus, the amino acid diffuses through the membrane into the organic extractant solution from which the amino acid can then be recovered.

The membrane ultrafiltration may be conducted using any membrane configuration, including flat sheet, spiral wound, hollow fiber, or tubular membranes. The flat sheet can be employed in a batch treatment process; it may also be employed in a continuous process where the flat sheet is fixed or spiral wound. These membranes are generally employed in continuous processes wherein the feed material (such as a fermentation broth containing the amino acid) flows parallel to the membrane surface and the amino acid permeates or diffuses through the pores of the membrane to the permeate or diffuse side. The flow of fluid is adjusted, so as to minimize fouling of the membrane resulting in a reduction of the amino acid permeating through the membrane.

This ultrafiltration process may be defined as a process of separating amino acids from an aqueous solution or suspension containing desired amino acid, cells, and undesired materials, comprising bringing said aqueous suspension into contact with one side or surface of a chemically resistant membrane, said membrane having micropores of a size sufficient for said amino acids to pass through, diffuse or permeate to the other side of said membrane. In ultrafiltration said membrane has micropores of a mean diameter less than about 0.2 micron, or a molecular weight cutoff of about 300,000.

Another process of treating said amino acid containing aqueous suspension is to bring said aqueous suspension into contact with a finely divided clay, clay like material, activated carbon or lime, which will adsorb at least a portion of the undesirable materials, and separating said finely divided materials and adsorbed undesirable materials from the remaining aqueous solution or suspension containing said amino acid. This treatment may be followed by the ultrafiltration process discussed immediately above or may be preceded by the ultrafiltration.

Either treatment tends to remove surfactant materials from the aqueous suspension, the presence of which tends to cause problems in phase disengagement in any subsequent extraction process employing a water immiscible organic solution containing a water insoluble extractant.

The extraction step with the water immiscible organic solution is as disclosed in commonly assigned co-pending Application Ser. No. 617,767 now U.S. Pat. No. 4,661,606, noted earlier, the disclosure of which is incorporated herein by reference.

After the extraction, the amino acid is found loaded into the organic phase from which the amino acid must be recovered. In Ser. No. 616,767 now U.S. Pat. No. 4,661,606, the amino acid is stripped from the organic phase either by use of a gaseous stripping agent or aqueous stripping agent. With a gaseous salt forming agent, a precipitate is formed and the precipitated amino acid salt is removed by conventional filtration methods. With an aqueous stripping agent the amino acid is released from the organic phase and transferred into the aqueous stripping phase from which the amino acid is then recovered by conventional means.

The present invention further encompasses other methods or processes of stripping or recovering the amino acid from the organic phase. One of the most preferred methods is stripping the loaded organic phase by contacting said organic phase with a concentrated acid, such as 85% $H_2SO_4$, in an amount sufficient to precipitate the amino acid. The amino acid under these conditions is insoluble in the organic phase and no identifiable aqueous phase results and the amino acid precipitates. In the absence of any aqueous phase, the process has the advantage of easy separation of the solid, precipitated amino acid from the liquid organic phase in contrast to a three phase system as described below.

Another adaptation of this recovery method is one in which the loaded organic phase is contacted with an aqueous solution already saturated with the amino acid, after which the sulfuric acid is added. The amino acid is insoluble in the organic and since the aqueous phase is already saturated also, the amino acid is also insoluble in the aqueous phase and precipitates. The amino acid may also be released from the organic extractant by use of an acidic aqueous stripping solution from which the amino acid is recovered by precipitation after the separation from the organic phase. In a cationic extractant system, the acidic stripping solution is added to provide one or more equivalents of acidic protons based on the amino acid in the organic solution. If one equivalent of acidic proton is used, the neutral amino acid is obtained; if more than one equivalent is used, either the salt or the neutral amino acid is obtained. About one equivalent, is most preferred. For anionic extraction systems, the acidic stripping solution is added to provide one extra equivalent of acidic protons and the precipitate is the amino acid salt.

There are two adaptations of this release of amino acid from the organic extractant solution resulting in transfer of the amino acid into an aqueous solution using aqueous acid solutions wherein the amino acid precipitates. These are based on two properties of the amino acid, particularly phenylalanine, which facilitates isolation from the aqueous stripping solution. The properties include increasing water solubility with increasing temperatures and increasing water solubility with decreasing pH below that at the isoelectric point.

The process based on temperature dependent solubility is conducted by stripping at an elevated temperature with an aqueous solution containing one equivalent of acidic protons based on the amino acid, such as phenylalanine, in the organic solution. The released phenylalanine is transferred into the aqueous solution at the pH at the isoelectric point, separated from the organic phase, and, if the process is conducted to effect sufficient concentration, the neutral amino acid precipitates when the aqueous solution is cooled.

The process based on pH dependent solubility can be conducted at any convenient temperature by stripping with an aqueous solution containing excess acid. Phenylalanine is released from the extractant and transferred into an aqueous solution at a pH below that at the isoelectric point. If the process is conducted to effect sufficient concentration, the neutral amino acid can be precipitated by adjusting the pH of the solution to that at the isoelectric point with a suitable base. Suitable bases for pH adjustment are the alkali metal hydroxides, ammonia or ammonium hydroxide. Suitable acids for stripping for both the temperature dependent and pH dependent process include the mono-, di-and triprotic acids with anions including the halides, $NO_3$, $ClO_4$, $BF_4$, $PF_6$, $SO_4$ and $PO_4$.

In still another variation of stripping from amino acid a loaded cationic extractant organic solution, the loaded organic is contacted with a brine at a pH greater than or equal to that at the isoelectric point. The amino acid is displaced from the extractant and transferred into the aqueous solution, from which it is precipitated.

The amino acid, such as phenylalanine, can be isolated from the aqueous solution as a neutral solid when the stripping process is conducted to provide sufficient concentration. If the pH of the brine is near that at the isoelectric point, stripping at an elevated temperature will provide a solution from which phenylalanine will precipitate upon cooling. If the pH of the brine is greater than that at the isoelectric point, stripping at any convenient temperature will provide a solution from which phenylalanine will precipitate upon adjustment of the pH to that at the isoelectric point.

Useful brines are solutions of salts for which the anion has some affinity for the cationic extractant. Examples include the alkali metal and alkaline earth metal halides and nitrates. The concentration of the brine solution should be such that substantial stripping is obtained. Thus, the higher the affinity of the anion for the cationic extractant, the lower the required concentration. Concentrations between 5 w/w% and saturation are useful. The pH of the brine solution can be adjusted to or above that at the isoelectric point with an alkali metal hydroxide.

In the preferred system, the concentration of phenylalanine or phenylalanate in the strip solutions should be >20 g/l to afford adequate recovery. There should be at least a 20° C. temperature differential between the stripping temperature and the precipitation temperature for the temperature dependent precipitation. Suitable acids for pH adjustment in the pH dependent precipitation include mono-, di- and triprotic acids with anions, including the halides, $SO_4$, $NO_3$, $ClO_4$, $BF_4$,$PO_4$ and $PF_6$. The most useful acids, however, are those containing the same anion as that of the salt used in the brine.

Accordingly, one aspect of the invention includes a method of stripping an organic extractant solution containing an amino acid comprising contacting said organic extractant solution with an aqueous stripping solution and precipitating said amino acid.

DETAILED DESCRIPTION AND PREFERRED EMBODIMENTS

As indicated earlier, the present invention involves an overall process which includes
(A) a pretreatment process prior to extraction
(B) extraction of the amino acid with an organic solution, and
(C) a process for recovery of the amino acid from the organic extractant solution.

The preferred pretreatment is an ultrafiltration employing a membrane having a molecular weight cut off high enough to permit passage of the amino acids, but low enough to prevent passage of other undesirable materials in the fermentation broth being treated.

The process is useful with fermentation broths containing at least one amino acid. It is particularly useful for the processing of lysine, phenylalanine or tryptophan fermentation broths. Generally these broths have already had the cellular material removed by conventional filtration, or other method, prior to treatment in accordance with the present invention, however, there may still be some cellular material present. The fermentation broths to which the invention is particularly applicable are those containing the desired amino acid (in typical concentrations above 1% to about 5%) and further composed as follows:

| Insoluble Component | Soluble Component |
|---|---|
| (a) Microorganisms | (x) Soluble Non-Utilized Raw materials |
| (b) Non-Utilized Raw Materials | (y) Soluble Metabolites |
| (c) Insoluble Salts | (1) Polysaccharides and sugars |
| (d) Immiscible Oils | (2) Proteins and Amino Acids |
| (e) Insoluble Metabolites | (3) Lipids |
| | (4) Nucleic Acids |

Membranes employed in the process, whether flat sheet, spiral wound, tubular or hollow fiber, are a wide variety of semi-permeable or permselective ultrafiltration membranes, which are effective to reject molecules having a molecular weight of over 300,000. The membrane may be described as "a semi-permeable membrane capable of concentrating amino acids", which term as used herein means a membrane system capable of rejecting molecules over 300,000 molecular weight. The membrane will have micropores permitting passage of the desired amino acid on the order of about 0.001 to about 0.2 microns, or a molecular weight range up to about 300,000. The preferred range nominal molecular weight cutoff (NMWC) is about 1000–100,000 molecular weight.

The materials from which the membrane are made are of a wide variety well known to those skilled in the membrane art. The more typical preferred materials, for example, cellulose acetate type; polysulfone, polyamide, fluoropolymers, polyolefinic polymers such as polypropylene. The material, of course, must be inert under conditions of use and the materials being treated. Membranes of polysulfone type are particularly useful in the present invention in treating amino acid containing fermentation broths.

In a typical cross flow ultrafiltration employing spiral wound, tubular or hollow fiber membrane, the fermentation broth flows parallel to the wall or surface of the membrane. The amino acid permeates or diffuses transverse to the membrane through the membrane to the permeate side of the membrane. The cross flow of the fermentation broth past the membrane is adjusted so as to minimize any deposition of undesired materials on the membrane, which tend to clog or foul the membrane and reduce the efficiency of the filtration. When the membrane is clogged, backflushing is needed to remove membrane fouling. The membrane is generally as thin as possible in order to avoid pressure drop across the membrane.

As indicated in the brief description an alternative treatment of the fermentation broth may be considered in lieu of the ultrafiltration, such as an adsorption treatment. This adsorption treatment may also be employed in combination with the ultrafiltration step, either before or after the ultrafiltration. Treatment prior to ultrafiltration is preferred, as it may minimize any problems with the ultrafiltration and particularly minimize the necessity for backwashing.

In this adsorption step, the fermentation broth is contacted with a finely divided material such as a clay or clay like material, activated carbon or lime. The particular treatment, whether ultrafiltration or adsorption or combination thereof, will large depend on the quality of the fermentation broth and components found therein. Both the adsorption treatment or the ultrafiltration remove materials which behave as surfactants which can cause problems in the subsequent extraction step, where good phase disengagement is desirable. Any surfactant present will tend to promote some emulsification with attendant phase disengagement problems.

The adsorbants which are utilized are commercially available materials. In general, all of the common, commercial crystalline clay minerals may be used such as the montmorillonite, kaolinite, hectorite and attapulgite. As a generality, clays vary considerably in composition depending upon the locality of the deposit. The preferred clays are the commercial bentonite clays which contain sufficient montmorillonite, such as 75%. Commercially available clays of this type are acid pH (acid activated) clays such as Filtrol Grade 1.

In the adsorption treatment, the fermentation broth is intimately mixed with the adsorbent and then filtered to remove the adsorbent and any other solids. After the adsorption treatment, the filtrate may then be subject to an ultrafiltration if such seems indicated. Generally, the adsorption step will be sufficient in itself and no ultrafiltration is necessary. Conversely, if ultrafiltration is employed, there is generally no need for the adsorbent treatment.

After the pretreatment of the broth, either by adsorption, ultrafiltration, or both, the aqueous broth containing the amino acid is then subjected to extraction employing a water insoluble extractant in solution in a water immiscible organic solvent. As indicated earlier, this extraction is conducted in accordance with commonly assigned, co-pending U.S. patent application Ser. No. 617,767, the disclosure of which was incorporated herein by reference, and which reference should be made for details contained therein. A brief discussion of the general extraction technique however follows.

Generally, amino acids can be extracted from aqueous solutions by a process comprising contacting an aqueous mixture containing amino acids with a water immiscible organic solution containing a water insoluble extractant, thereby forming two phases and separating the two phases after amino acids have transferred into the organic phase. With the adsorption or ultrafiltration treatment discussed earlier, phase disengagement of the two phases is clear, sharp and rapid.

While a number of extractants are disclosed in the commonly assigned Application, the preferred extractants are certain quaternary ammonium compounds (cationic) or certain organic sulfonic acids (anionic). The quaternary ammonium compounds are those of the formula

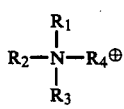

where $R_1$, $R_2$, $R_3$ and $R_4$ individually are aliphatic hydrocarbon groups containing from about 1 to about 22 carbon atoms and where $R_1$, $R_2$, $R_3$ and $R_4$ together have a minimum of 25 carbon atoms, and where at least three groups selected from the group consisting of $R_1$, $R_2$, $R_3$ and $R_4$ are at least a $C_4$.

Suitable sulfonic acid extractants are those having the formula

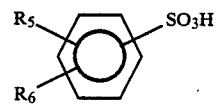

where $R_5$ and $R_6$ are aliphatic hydrocarbon groups about 6 to about 22 carbon atoms, where $R_5$ and $R_6$ together contain at least 18 carbon atoms, and where neither $R_5$ nor $R_6$ are smaller than a $C_6$; and organic sulfonic acids having the structural formula:

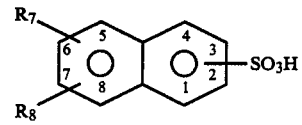

where $R_7$ and $R_8$ are aliphatic hydrocarbon groups containing from about 4 to about 22 carbon atoms, where $R_7$, $R_8$, or the sulfonic group may be attached to positions 1-8 on the aromatic rings, and where neither $R_7$ nor $R_8$ is smaller than a $C_4$, and where $R_7$ and $R_8$ together have at least 18 carbon atoms.

These extractants are not only essentially water insoluble, but are soluble in non-polar water immiscible organic solvents. When these extractants are dissolved in the non-polar solvent, amino acids are extracted from the immiscible aqueous (polar) phase that it is contacted with.

The quaternary ammonium compounds and sulfonic acids defined above are well known and commonly recognized by those in the extraction art. Further, such compounds are commercially available or are easily prepared by known methods. The quaternary ammonium compounds are cationic extractants soluble in water immiscible organic solvents. Illustrative of such are found in U.S. Pat. Nos. 3,455,816; 4,128,493; 3,215,620 and 3,215,621. Commercially available quaternary compounds are also disclosed in General Technical Bulletin 12-A-2 of General Mills, of January 1966 entitled "Fatty Nitrogen Chemicals for Industry", which describe "ALIQUAT ®" quaternary ammonium compounds containing mono-, di- and trifatty alkyl groups.

The sulfonic acids defined above are anionic extractants and are also well known compounds either available commercially or can be made by conventional, known technology. U.S. Pat. No. 4,160,0807, which makes reference to sulfonic acids from which the patentee prepares his desired sulfonamido oximes.

In order to be extracted in accordance with the process of the instant invention, the amino acid being removed from the aqueous mixture must not be in its zwitterion form. This zwitterion is that form of an amino acid where the amino acid molecule contains both a positive and negative charge. This form, which will vary slightly with the specific amino acid in solution, occurs in an aqueous solution over the more neutral pH ranges (from about 4.5 to 7.5). To extract amino acids therefore, the instant invention generally requires the aqueous mixture containing amino acids to have an acidic pH value of about 4.5 or less (preferably less than 3.0), or a basic pH value of about 7.5 or more so that the amino acids are predominately not zwitterions. Alternatively stated, the amino acids must be in an aqueous (polar) phase having a pH such that the amino acids are either cationic or anionic.

Acid or base can be added to the aqueous mixture in order to maintain the pH at the right level. Suitable acids to be used for pH control in the aqueous mixture are mineral acids, and suitable bases to be used are alkali and alkali earth metal hydroxide and ammonium hydroxide bases. The stronger acids and bases which tend to be soluble in water and insoluble in the organic phase are preferred; such acids are hydrochloric, hydrofluoric, nitric, sulfuric, hydrobromic and phosphoric. Phosphoric acid is a good acidifying agent for the aqueous phase. Suitable bases for pH control in the aqueous phase include alkali metal or alkaline earth metal bases, particularly potassium hydroxide, sodium hydroxide, ammonium hydroxide and sodium carbonate.

General extractions of overall amino acids from fermentation broths and other aqueous mixtures can also be accomplished. In this instance an overall and substantially complete removal of amino acids from the aqueous mixture is desired. Acceptably, the ratio of extractant concentration to amino acid concentration is 1:1 on a molar basis. Preferably, the ratio should be from about 1.2 moles of extractant per amino acid molar concentration, to about 10 moles of extractant per total moles of amino acid. However, the concentration of extractant can be limited to less than 1 mole per mole of amino acids in order to extract more preferentially one amino acid over another. Thus, the ratio of the number of moles of extractant in the organic solution to the number of moles of amino acids in the aqueous solution will generally be in the range of from about 0.25–10 moles of extractant per mole of amino acid, more desirably a molar ratio of 1:1 to 2:1.

The respective volumes of the phases are generally determined by individual need, such as the type of extraction system used, and the respective concentrations of the solutions. Since amino acids must frequently be extracted from very dilute aqueous solutions, the organic to aqueous volume ratio can acceptably vary from about 1:20 to about 20:1. More desirably, a more effective range for the ratio of the organic phase volume to the aqueous phase volume is from about 1:5 (organic to aqueous) to about 5:1 (organic to aqueous). A more preferred ratio for the organic phase volume to the aqueous phase volume, especially in commercial extraction systems is from about 1:3 to about 3:1.

The organic extractant phase should contact the aqueous amino acid phase for a sufficient length of time to permit the amino acids to enter the organic phase. The time of contact depends on the particular system, the type of equipment used, and upon individual needs and desires. As a general rule, however, the contact time between the organic extractant solution and the aqueous amino acid mixture should be in excess of 0.1 seconds with some equipment, but generally less than 3 hours. Naturally a minimum contact time is desired, thus a more desirable phase contact time would be in the range of from about 5 seconds to one hour while a more preferred contact time is from about 5 seconds to about 10 minutes.

Any substantially water immiscible liquid solvent can be used in the process of the instant invention. Typically, this includes aliphatic and aromatic hydrocarbons. Aliphatic hydrocarbons such as alkanes, including cycloalkanes and halogenated alkanes are suitable; preferred alkanes have a minimum of five carbon atoms; preferred halogenated alkanes have a minimum of two carbon atoms; aromatic hydrocarbons which can be used include benzene, and substituted products such as toluenes, xylenes and cumene. Also suitable as a solvent are those esters, ethers, ketones, and alcohols which are substantially water immiscible. Furthermore any blend of these substances or a water immiscible kerosene is also suitable. Preferred organic solvents for use in the amino acid recovery processes are the aliphatic and aromatic hydrocarbons having flash points of 150° F. and higher and solubilities in water of less than 0.1% by weight. These solvents are also essentially non-toxic and chemically inert and the costs thereof are currently within practical range. Representative commercially available solvents are: Kermac 470B (an aliphatic kerosene available from Kerr-McGee—Flash Point 175° F.), Chevron Ion Exchange Solvent (available from Standard Oil of California—Flash Point 195° F.), Escaid 100 and 110 (available from Exxon-Europe—Flash Point $\approx 180°$ F.), Norpar 12 (available from Exxon-U.S.A.—Flash Point 160° F.), Conoco C-1214L (available from Conoco—Flash Point 160° F.), Aromatic 150 (an aromatic kerosene available from Exxon-U.S.A.—Flash Point 150° F.) and various other kerosenes and petroleum fractions available from other oil companies.

Modifiers can be added to the solvent in addition to the extractant in order to modify or improve the extraction of amino acids. Substances, which are preferred as modifiers are alcohols in the range of from about 10 to about 13 carbon atoms and phenols such as the alkyl (8–12 carbon atom) substituted phenols, can be added to improve solubility, phase separation and/or other important characteristics of the organic solution.

The extraction process is preferably conducted in a countercurrent continuous process, but may be conducted in a batch process. Generally, the extraction is conducted employing one extractant and at one pH level. However, a two stage extraction process may be employed, in which an extraction is conducted in a first pass at a low pH, followed by extraction at a higher pH. Such a process will generally employ a quaternary ammonium extractant of the type described earlier. In any event, the extraction process provides an organic solution of the extractant, which contains the amino acid from which the amino acid must be removed and recovered. In the commonly assigned, co-pending application noted earlier, this removal was carried out (a) using an acid or basic gas to precipitate the amino acid from the organic solution; or (b) contacting the organic solution phase with an aqueous stripping solution, whereby the amino acid is transferred from the water immiscible organic solution into the aqueous stripping solution.

In the latter, two phases which are immiscible are provided, which can then be separated. The organic phase is then returned to the circuit for extraction and the aqueous phase now containing the amino acid in higher concentration is treated by any conventional method, such as precipitation, crystallization and the like to recover the amino acid.

In the present invention, other methods were found by which the amino acid can be removed from the organic phase. Thus, the present invention is concerned with an improved method of removal of amino acid from water immiscible organic solutions of a water insoluble extractant containing an amino acid. In each of these, an aqueous stripping solution is employed and the amino acid is precipitated, in which form it can be recovered in solid form by simple filtration or separation technique. The removal of the amino acid from the organic solution may be carried out in any of four different variations described below:

(a) contacting the organic solution containing the amino acid with a concentrated acid solution, such as 85% sulfuric acid, in an amount to precipitate the amino acid, in the absence of any aqueous phase;

(b) contacting the organic solution containing the amino acid with an aqueous acidic solution saturated with the amino acid whereby the amino acid precipitates being insoluble in the organic and the aqueous phases;

(c) contacting the organic solution containing the amino acid with an aqueous acidic solution, whereby the amino acid is transferred to the aqueous acidic phase, which is separated from the organic phase, and precipitating the amino acid from the aqueous phase by adjusting the temperature or the pH level so as to precipitate the amino acid;

(d) contacting the organic solution containing the amino acid with a brine at a pH greater than or equal to that at the isoelectric point whereby the amino acid is displaced from the extractant in the organic solution and transferred to the aqueous solution.

In variation (a) above, the amino acid is precipitated from the organic extractant solution containing the amino acid by contacting the water immiscible organic solution with a concentrated acid solution in an amount sufficient to precipitate the amino acid. Concentrated acid solutions of acids, such as sulfuric acid, phosphoric acid, hydrohalide such as hydrochloric or hydrobromic, tetrafluoroboric, hexafluorophosphoric, nitric, trifluoroacetic and oxalic are representative of those which are employed.

In variation (b), the same acids noted in (a) may be employed. In the variation, three phases are present:
(1) the organic phase
(2) aqueous phase saturated with the amino acid; and
(3) a solid amino acid phase.

The solid phase may be removed by filtration or centrifugation leaving the two immiscible organic and aqueous phases, which can be separated and recycled for use in the circuit.

In variation (c), the amino acids are released from the extractant and transferred into an aqueous solution using aqueous acid stripping solutions.

For cationic extractant systems, the acidic stripping solution is added to provide one or more equivalents of acidic protons based on amin acid in the organic solution, If one equivalent of acidic protons is used, the neutral amino acid is obtained; if more than one equivalent is used, either the salt or the neutral amino acid is obtained. For anionic extractant systems, the acidic stripping solution is added to provide one extra equivalent of acidic protons and the precipitate is the amino acid salt.

Two properties of the amino acid facilitate its isolation from the aqueous stripping solutions. The properties include increasing water solubility with increasing temperature and increasing water solubility with decreasing pH below that at the isoelectric point.

The process based on temperature dependent solubility is conducted by stripping at an elevated temperature with an aqueous solution containing one equivalent of acidic protons based on the amino acid in the organic solution. The released amino acid is transferred into the aqueous solution at the pH at isoelectric point, which is separated from the organic phase and, if the process is conducted to effect sufficient concentration, the neutral amino acid precipitates when the aqueous solution is cooled. The preferred process would be conducted with a least a 20° C. differential between stripping temperature and precipitation temperature and the concentration of phenylalanine in the strip solution before cooling would be >20 g/l. Suitable acids for such stripping include mono-, di and triprotic acid with anions including the halides, $NO_3$, $ClO_4$, $BF_4$, $PF_6$, $SO_4$ and $PO_4$.

The process based on pH dependent solubility can be conducted at any convenient temperature by stripping with an aqueous solution containing excess acid. The amino acid is released from the extractant and transferred into an aqueous solution at a pH below that at the isoelectric point. If the process is conducted to effect sufficient concentration, the neutral amino acid can be precipitated by adjusting the pH of the solution to that at the isoelectric point with a suitable base. In the preferred process, the amount of acid in the stripping solutions would be at least a two-fold molar excess based on phenylalanine and the concentration of phenylalanine in the strip solution before pH adjustment would be >20 g/l. Suitable acids are the same as described for the temperature dependent process. Suitable bases for pH adjustment are the alkali metal hydroxides.

Variation (d) is particularly useful in removing or stripping the amino acid from loaded cationic extractant organic solutions. In this variation, the the loaded organic is contacted with a brine at a pH greater than or equal to that at the isoelectric point and the amino acid is displaced from the extractant and transferred into the aqueous solution.

The amino acid, particularly phenylalanine, can be isolated from the aqueous solution as a neutral solid when the stripping process is conducted to provide sufficient concentration. If the pH of the brine is near that at the isoelectric point, stripping at an elevated temperature will provide a solution from which the amino acid will precipitate upon cooling. If the pH of the brine is greater than that at the isoelectric point, stripping at any convenient temperature will provide a solution from which the amino acid will precipitate upon adjustment of the pH to that at the isoelectric point.

Useful brines are solutions of salts for which the anion has some affinity for the cationic extractant. Examples include the alkali metal (such as Na or K) and alkaline earth metal (such as Ca and Mg) halides and nitrates. The concentration of the brine solution should be such that substantial stripping is obtained. Thus, the higher the affinity of the anion for the cationic extractant, the lower the required concentration. Concentrations between 5 w/w% and saturation are useful. The pH of the brine solution can be adjusted to or above that at the isoelectric point with a base such as an alkali metal or alkaline earth metal hydroxide, ammonium hydroxide, sodium carbonate and the like.

In the preferred system, with phenylalanine, the concentration of phenylalanine or phenylalanate n the strip solutions should be >20 g/l to afford adequate recovery. There should be at least a 20° C. temperature differential between the stripping temperature and the precipitation temperature for the temperature dependent precipitation. Suitable acids for pH adjustment in the pH dependent precipitation include mono-, di- and triprotic acids with anions, including the halides, $SO_4$, $NO_3$, $ClO_4$, $BF_4$ and $PF_6$. The most useful acids, however, are those containing the same anion as that of the salt used in the brine.

The following examples serve to illustrate, but not limit, the invention. All parts and percentages are by weight, unless otherwise noted.

In the examples, the fermentation broths used were a phenylalanine (hereinafter PHE) and a lysine (hereinafter LYS) fermentation broth typically containing about 3% amino acid. Otherwise, chemicals and equipment used were as follows:

| Chemical or Equipment: | Available From: |
|---|---|
| Methyltricaprylammonium Chloride (ALIQUAT ® 336) | Henkel Corporation |
| Dinonylnaphthalene Sulfonic Acid | King Industries |
| Decalin (cis, trans-decahydronaphthalene) | E. I. duPont de Nemours & Co. |
| Low-Aromatic Kerosene (ESCAID 110) | Exxon Chemicals |
| Tridecyl Alcohol | Exxon Chemicals |
| 1,2-Dichloroethane | Aldrich Chemicals |
| Clay (Filtrol Grade 1) | Filtrol |
| Activated Carbon (Norit A) | Matheson Coleman & Bell |
| Lime (CaO) | Matheson Coleman & Bell |
| Cross flow Filtration Membranes | Millipore Corporation |
| Dialysis Membrane Tubing | Spectrum Medical Industries |

In the examples, the quaternary ammonium sulfate organic extractant solution was prepared by dissolving methyltricaprylammonium chloride (135 g/l) and tridecyl alcohol (150 g/l) in decalin or low-aromatic kerosene and washing the resulting solution with several one volume portions of aqueous sodium sulfate (100 g/l). The sulfonic acid organic extractant solution was prepared by dissolving dinonylnaphthalene sulfonic acid (150 g/l) in 1,2-dichloroethane.

PART I

Broth Pretreatment

Example 1

This example is a control to illustrate the phase disengagement typically required when no adsorbent or ultrafiltration was employed. Using only simple filtration of the PHE fermentation broth to remove insolubles, the pH was adjusted to pH 11 by adding 50% sodium hydroxide and the sample was filtered. Phase disengagement was assessed by shaking the sample (1.0 part) and quaternary ammonium sulfate organic extractant solution (1.0 part) together for 10 minutes and transferring the mixture to a separatory funnel. Phase disengagement typically required between 15 minutes and 24 hours. The resulting mixtures typically contained large amounts of insoluble material at the interface.

A. Adsorbent Treatment Examples

Example 2

PHE fermentation broth (100 parts) was stirred vigorously with clay (1 part) for 30 minutes and the mixture was filtered. Phase disengagement was assessed as described in Example 1 and less than 5 minutes was required to give a mixture with clean, well-defined interface.

Example 3

PHE fermentation broth (100 parts) was stirred vigorously with activated carbon (1 part) for 30 minutes and the mixture was filtered. Phase disengagement was assessed as described in Example 1 and less than 5 minutes was required to give a mixture with a clean, well-defined interface.

Example 4

PHE fermentation broth (100 parts) was stirred vigorously with lime (1 part) for 30 minutes and the mixture was filtered. Phase disengagement was assessed as described in Example 1 and less than 10 minutes was required to give a mixture with only a small amount of insoluble material at the interface.

B. Ultrafiltration Treatment Examples

Example 5

A series of experiments was conducted in which PHE fermentation broth was filtered in a cross flow mode using commercially available filtration equipment. PHE fermentation broth was prefiltered to remove insolubles and cross flow filtered. The filtration was continued until a specified percentage of the feed had been collected as filtrate. In two-stage filtration experiments, the retentate was then diluted to a specified volume with deionized water and the filtration process was repeated until a second specified percentage had been collected as filtrate. The two filtrates were combined. In five-stage filtration experiments, dilution of retentate and filtration was repeated four times after the first filtration. Phase disengagement was assessed in all cases as described in Example 1. The results are given in Table I below.

TABLE I

| Membrane NMWC | Number of Stages | % First Filtrate | Retentate Dilution | % Subsequent Filtrates | Phase Disengagement* |
|---|---|---|---|---|---|
| 1,000 | 2 | 60 | 1.5 | 60 | A |
| 10,000 | 5 | 90 | 1.0 | 50 | A |
| 30,000 | 2 | 80 | 4.0 | 70 | B |
| 100,000 | 5 | 90 | 1.0 | 50 | B |
| 300,000 | 1 | 90 | — | — | B |

*A = Phase Disengagement within 5 minutes to give a mixture with clean, well-defined interface;
B = Phase Disengagement within 5 minutes to give a mixture with a small amount of insoluble material at the interface

EXAMPLE 6

PHE fermentation broth was filtered to remove insolubles. The sample was sealed in dialysis membrane tubing (nominal molecular weight cutoff $\approx 1,000$) and immersed in an equal volume of deionized water with stirring for 16 hours. Phase disengagement was assessed as described in Example 1 and less than 5 minutes was required to give a mixture with a clean, well-defined interface.

EXAMPLE 7

A sample of LYS fermentation broth was filtered to remove insolubles. The sample (1.0 part) was diluted with deionized water (1.0 part) and the pH was adjusted to pH 1.4 by adding sulfuric acid. Phase disengagement was assessed by shaking the sample (1.0 part) and sulfonic acid organic extractant solution (1.0 part) together for 5 minutes in a separatory funnel. Phase disengagement required 2 to 3 hours.

EXAMPLE 8

LYS fermentation broth (1.0 part) was sealed in dialysis membrane tubing (nominal molecular weight cutoff ≈1,000) and immersed in deionized water (4.0 parts) with stirring for 6 hours. The pH of the permeate was adjusted to pH 1.4 by adding sulfuric acid and phase disengagement was assessed as described in Example 8. Phase disengagement required 30 minutes.

PART II

Stripping

In these examples, the chemicals and equipment were as specified above in Part I. In these examples, the loaded organic extractant solution was prepared by:

(1) shaking a sample of quaternary ammonium sulfate organic extractant solution (1.0 part) with PHE fermentation broth, which was cross flow filtered (nominal molecular weight cutoff of 10,000) and subsequently adjusted to pH 11 (1.0 part) for 10 to 15 minutes and separating the phases; or (2) countercurrent extraction of PHE from cross flow filtered PHE fermentation broth (10,000 nominal molecular weight cutoff) and subsequently adjusted to pH 11 with quaternary ammonium sulfate organic extraction solution at a phase ratio of 1:1 in a one-inch York-Scheibel extraction column.

Example 9

A series of experiments was conducted in which the concentration of a sulfuric acid stripping solution was varied (mol $H^+$/PHE≈1.0). The PHE loaded organic was placed in a beaker with a magnetic stirring bar and the stripping solution was added with vigorous stirring. Precipitate formed immediately. Stirring was continued for 30–45 minutes and the solid was isolated by filtration or centrifugation, washed with hexane and air-dried. The results of the experiments are given in Table II below in which no aqueous phase was present at concentrations of 25 to 100.

TABLE II

| $H_2SO_4$ Concentration | % PHE Recovered To: | |
|---|---|---|
| | Solid | Organic |
| 100 | 76 | 22 |
| 85 | 86 | 17 |
| 77 | 75 | 20 |
| 50 | 76 | 23 |
| 25 | 81 | 19 |
| 10 | 70* | 25* |
| 5 | 60+ | 22+ |

*1% PHE recovered to aqueous phase
+7% PHE recovered to aqueous phase

In Examples 10–13 below, concentrated acid is employed as described in variation (a), and no separate aqueous phase forms.

Example 10

A series of experiments was conducted in which the mole ratio of acidic protons to PHE in the loaded organic was varied (mole $H^+$/PHE≈0.4–2.4). The PHE loaded organic was placed in a beaker with a magnet stirring bar and the sulfuric acid stripping solution (85% $H_2SO_4$) was added with vigorous stirring. Precipitate formed immediately. Stirring was continued for 30–45 minutes and the solid was isolated by filtration or centrifugation, washed with hexane and air-dried. The results of the experiments are given in Table III below.

TABLE III

| Mole Ratio | % PHE Recovered To: | |
|---|---|---|
| | Solid | Organic |
| 0.4 | 18 | 86 |
| 0.8 | 50 | 57 |
| 1.0 | 86 | 17 |
| 1.2 | 86 | 27 |
| 1.6 | 89 | 22 |
| 2.0 | 90 | 22 |
| 2.4 | 77 | 12 |

Example 11

PHE loaded organic (1.53% PHE, 330 parts) was placed in a beaker with a magnetic stirring bar and phosphoric acid (b 85%, 1.0 part) was added with vigorous stirring. Precipitate formed within 1 minute. Stirring was continued for 30–45 minutes and the solid was isolated by filtration, washed with hexane and air-dried. Recovery of PHE to solid was 55% and to stripped organic was 58%.

Example 12

PHE loaded organic (1.53% PHE, 120 parts) was placed in a beaker with a magnetic stirring bar and hydrochloric acid (38%, 1.0 part) was added with vigorous stirring. Precipitate formed with 1 minute. Stirring was continued for 30–45 minutes and the solid was isolated by filtration, washed with hexane and air-dried. Recovery of PHE to solid was 54% and to stripped organic was 44%.

Example 13

A sample of quaternary ammonium sulfate organic extractant solution (1.0 part) was contacted with three successive portions of a solution of tryptophan (2.0 parts) at pH 12.5. The loaded organic contained 5.1% tryptophan. Loaded organic (130 parts) was placed in a beaker with a magnetic stirring bar and the sulfuric acid stripping solution (85% $H_2SO_4$, 1.0 part) was added with vigorous stirring. Precipitate formed immediately. Stirring was continued for 30 minutes and the mixture was cooled at 0° C. for 16 hours. The solid was isolated by filtration or centrifugation, washed with hexane and air-dried. Recovery of tryptophan to solid was 79%.

In Examples 14 and 15 below, the organic extractant solution consisted of ALIQUAT® 336 (45 g/l) and tridecyl alcohol (50 g/l) in decalin. The organic solution (200 ml) was contacted successively with three equal volumes of a ph 12.5 solution of phenylalanine (25 g/l) in deionized water. The loaded organic solution was filtered to remove entrained aqueous. The resulting solution typically contained 14 g/l.

Example 14

A mixture of loaded organic extractant solution (200 ml) and 20% hydrochloric acid (100 ml) was shaken vigorously for 30 minutes. The layers were separated and the pH of the aqueous layer was adjusted to pH 5.9±0.1 using 45% sodium hydroxide. After cooling to 0° C., a white solid precipitated. The solid was isolated by filtration and washed with hexanes (2×50 ml). The solid was identified as neutral phenylalanine by infrared and NMR. The recovery of solid phenylalanine in stripping was 35.7%. The filtrate contained phenylalanine at 17.6 g/l.

Example 15

The loaded organic extractant solution (200 ml) was stirred vigorously and 85 w/w % aqueous sulfuric acid (1.0 g) was added. A white solid precipitated immediately upon addition. The mixture was cooled to 0° C., the precipitated solid was isolated by filtration and washed with hexane (2×50 ml). The recovery in the stripping step is >95% and the solid was neutral phenylalanine by infrared analysis.

Example 16

A stripping solution was prepared by adding sulfuric acid (85%, 1.0 part) to a solution of PHE in deionized water (3.00% PHE, 250 parts). The stripping solution was added to PHE loaded organic (1.57% PHE, 250 parts) in a beaker with vigorous stirring. The mixture was stirred for 30 minutes, allowed to stand for 1 hour and filtered to isolate the precipitate PHE. The recovery of PHE as solid was 54%. The stripped organic contained 0.34% PHE and the aqueous phase contained 3.31% PHE.

Example 17

This example illustrates the use of a brine. A 210 ml portion of an organic solution consisting of ALIQUAT® 336 (45 g/l) and tridecyl alcohol (50 g/l) in decalin was contacted successively with three 200 ml portions of a pH 12.5 solution of phenylalanine (25 g/l) in deionized water. The loaded organic was filtered to remove entrained aqueous. The resulting solution typically contained 14 g/l phenylalanine.

The striping solution consisted of sodium chloride (200 g/l) in deionized water. Sodium hydroxide (45%) was added to raise the pH to pH 12.5. The loaded organic was contacted with a 70 ml portion of the stripping solution. The resulting brine solution contained 32 g/l phenylalanine. The brine solution was warmed to ~35° C. and the pH was adjusted to pH 5.9±0.1 using concentrated hydrochloric acid. The mixture was cooled to 0° C., the solid was isolated by filtration and washed with hexanes (2×50 ml). The filtered brine contained 2.5 g/l phenylalanine and the solid was 3.2 g of phenylalanine. The identity of the product was confirmed by infrared spectroscopy.

We claim:

1. In a process of recovering an amino acid from an aqueous solution containing said amino acid which comprises extracting said amino acid with a water immiscible organic solution of a water insoluble extractant whereby an aqueous phase and an organic phase forms which phases are immiscible and which disengage and are separated, and recovering said amino acid from said water immiscible organic solution, the improvement comprising treating said aqueous amino acid containing solution prior to said extraction with a process selected from the group consisting of
   (a) ultrafiltration
   (b) adsorption and
   (c) a combination of (a) and (b);
wherein said amino acid is a naturally occurring amino acid, and said ultrafiltration comprises having said aqueous solution contact a semipermeable membrane containing micropores with a mean micropore diameter less than 0.2 micron, sufficient to permit passage of said amino acid and prevent passage of undesired materials in said aqueous solution affecting phase disengagement in said extraction, to provide a diffusate or permeate containing said amino acid; and extracting said amino acid from said aqueous solution with a water immiscible organic solution of a water insoluble extractant to form an aqueous phase and an organic phase immiscible therewith, which phases disengage in a lesser time than such phases would disengage if said treatment prior to said extraction were not conducted, wherein said extractant is selected from the group consisting of:

(x) a cationic extractant having a quaternary ammonium ion of the formula:

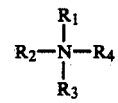

where $R_1$, $R_2$, $R_3$ and $R_4$ individually are aliphatic hydrocarbon groups containing from about 1 to about 22 carbon atoms and where $R_1$, $R_2$, $R_3$ and $R_4$ together have a minimum of 25 carbon atoms, and where at least three groups selected from the group consisting of $R_1$, $R_2$, $R_3$ and $R_4$ are at least a $C_4$; and (y) an anionic sulfonic acid selected from the group consisting of organic sulfonic acids having the structural formula:

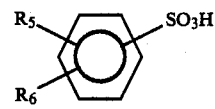

where $R_5$ and $R_6$ are aliphatic hydrocarbon groups individually having from about 6 to about 22 carbon atoms, where $R_5$ and $R_6$ together contain at least 18 carbon atoms, and organic sulfonic acids having the structural formula:

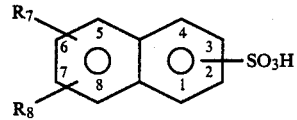

where $R_7$ and $R_8$ are aliphatic groups containing from about 4 to about 22 carbon atoms; where $R_7$ and $R_8$, or the sulfonic group may be attached to positions 1–8 on the aromatic rings, and where $R_7$ and $R_8$ together have at least 18 carbon atoms;

and said amino acid is recovered from said water immiscible organic solution of said water insoluble extractant by contacting said water immiscible solution with an acid.

2. In a process as defined in claim 1, wherein said membrane is tubular and said aqueous mixture flows parallel to the walls of said membrane and said amino acid permeates or diffuses through said micropores transverse to the walls of said membrane, providing a permeate containing said amino acid.

3. In a process as defined in claim 1 wherein said aqueous solution is a lysine fermentation broth.

4. In a process as defined in claim 1 wherein said aqueous solution is a phenylalanine fermentation broth.

5. In a process as defined in claim 1 wherein said aqueous solution is a tryptophan fermentation broth.

6. In a process as defined in claim 1, wherein said membrane is a polysulfone or cellulose polymer.

7. In a process as defined in claim 2 wherein said tubular membrane has a nominal molecular weight cut-off up to 300,000.

8. In a process as defined in claim 1 wherein said amino acid is selected from the group consisting of arginine, histidine, isoleucine, leucine, lysine, methionine, phenylalanine, threonine, tryptophan, β-alanine, tyrosine, glutamic acid and aspartic acid.

9. In a process as defined in claim 1 wherein said amino acid is phenylalanine.

10. In a process as defined in claim 1 wherein said quaternary ammonium compound is methyltricaprylyl ammonium chloride.

11. In a process as defined in claim 1 wherein said quaternary ammonium compound is methyltricaprylyl ammonium sulfate.

12. In a process as defined in claim 1 wherein said sulfonic acid is dinonylnaphthalene sulfonic acid.

13. In a process as defined in claim 1 wherein the solvent in said organic solution containing said extractant is selected from the group consisting of water immiscible aliphatic hydrocarbons, aromatic hydrocarbons, halogenated hydrocarbons, esters, ethers, ketones and alcohols.

14. In a process as defined in claim 1 wherein the solvent in said organic solution containing said extractant is kerosene.

15. In a process as defined in claim 1 wherein said adsorption comprises contacting said aqueous solution containing said amino acid with an adsorbant whereby undesirable materials in said aqueous solution are adsorbed.

16. In a process as defined in claim 15 wherein said adsorbant is selected from the group consisting of clay, activated charcoal and lime.

17. In a process as defined in claim 15 wherein said adsorption is conducted prior to ultrafiltration.

18. In a process as defined in claim 15 wherein said adsorbant is a montmorillonite clay.

19. In a process as defined in claim 15 wherein said adsorption is conducted after said ultrafiltration.

20. In a process as defined in claim 1 wherein said amino acid in said water immiscible organic solution is recovered by stripping and precipitating said amino acids from said organic solution.

21. In a process as defined in claim 20 wherein said water immiscible organic solution containing the extracted amino acid is contacted with a concentrated acid thereby stripping and precipitating said amino acid.

22. In a process as defined in claim 21 wherein said concentrated acid is 85% sulfuric acid.

23. In a process as defined in claim 21 wherein said concentrated acid is 38% hydrochloric acid.

24. In a process as defined in claim 21 wherein said acid is 85% phosphoric acid.

25. In a process as defined in claim 20 wherein said water immiscible organic solution containing the extracted amino acid is contacted with an acidic aqueous stripping solution saturated with said amino acid to which about 1 or more equivalents of acidic proton is added.

26. In a process as defined in claim 25 wherein said extractant is a cationic extractant and about 1 equivalent of acidic proton is added whereby the neutral amino acid is precipitated.

27. In a process as defined in claim 25 wherein said extractant is a cationic extractant and more than one equivalent of acidic proton is added.

28. In a process as defined in claim 25 wherein said extractant is an anionic extractant and about 1 equivalent excess of acidic protons is added and the salt of said amino acid is precipitated.

29. In a process as defined in claim 20 wherein said water immiscible organic solution containing the extracted amino acid is contacted with an aqueous acidic stripping solution containing about one equivalent or more of acidic proton based on the amino acid in said organic solution at a first temperature whereby said amino acid is transferred from said organic solution into said aqueous stripping solution at a pH at the isoelectric point, separating said aqueous solution from said organic solution and reducing the temperature at least 20° C. below the first stripping temperature whereby said amino acid precipitates.

30. In a process as defined in claim 20 wherein said water immiscible organic solution containing the extracted amino acid is contacted with an aqueous acidic stripping solution containing a molar excess of acid based on said amino acid whereby said amino acid is transferred from said organic solution into said aqueous stripping solution at a pH below the isoelectric point and adjusting the pH to the isoelectric point whereby said amino acid precipitates.

31. In a process as defined in claim 20 wherein said water immiscible organic solution containing the extracted amino acid is contacted with a brine at a pH greater than or equal to the isoelectric point whereby said amino acid is transferred from said organic extractant solution into said brine and precipitating said amino acid from said brine.

32. In a process as defined in claim 31 wherein the pH of said brine is at the isoelectric point and said amino acid is precipitated by reducing the temperature by at least 20° C. below the stripping temperature.

33. In a process as defined in claim 31 wherein the pH of said brine is greater than the isoelectric point and said amino acid is precipitated by adjusting the pH to the isoelectric point.

* * * * *